US00PP32667P2

(12) United States Plant Patent
Meulenbroek

(10) Patent No.: US PP32,667 P2
(45) Date of Patent: Dec. 22, 2020

(54) STRAWBERRY PLANT NAMED 'FS 1705'

(50) Latin Name: ***Fragaria* x *ananassa***
Varietal Denomination: FS 1705

(71) Applicant: Egbertus Joseph Meulenbroek, Zetten (NL)

(72) Inventor: Egbertus Joseph Meulenbroek, Zetten (NL)

(73) Assignee: FRESH FORWARD HOLDING, B.V., Eck en Wiel (NL)

( * ) Notice: Subject to any disclaimer, the term of this patent is extended or adjusted under 35 U.S.C. 154(b) by 0 days.

(21) Appl. No.: 16/873,040

(22) Filed: Jan. 21, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

*Primary Examiner* — Susan McCormick Ewoldt
(74) *Attorney, Agent, or Firm* — C. A. Whealy

(57) ABSTRACT

A new and distinct cultivar of Strawberry plant named 'FS 1705', characterized by its compact, upright to semi-upright plant habit; moderately vigorous to vigorous growth habit; early and uniform fruit ripening; medium to large-sized conical fruits that are glossy and orange red in color; pleasant fruit aroma and sweet taste; and excellent fruit postharvest longevity.

2 Drawing Sheets

Figure 1:
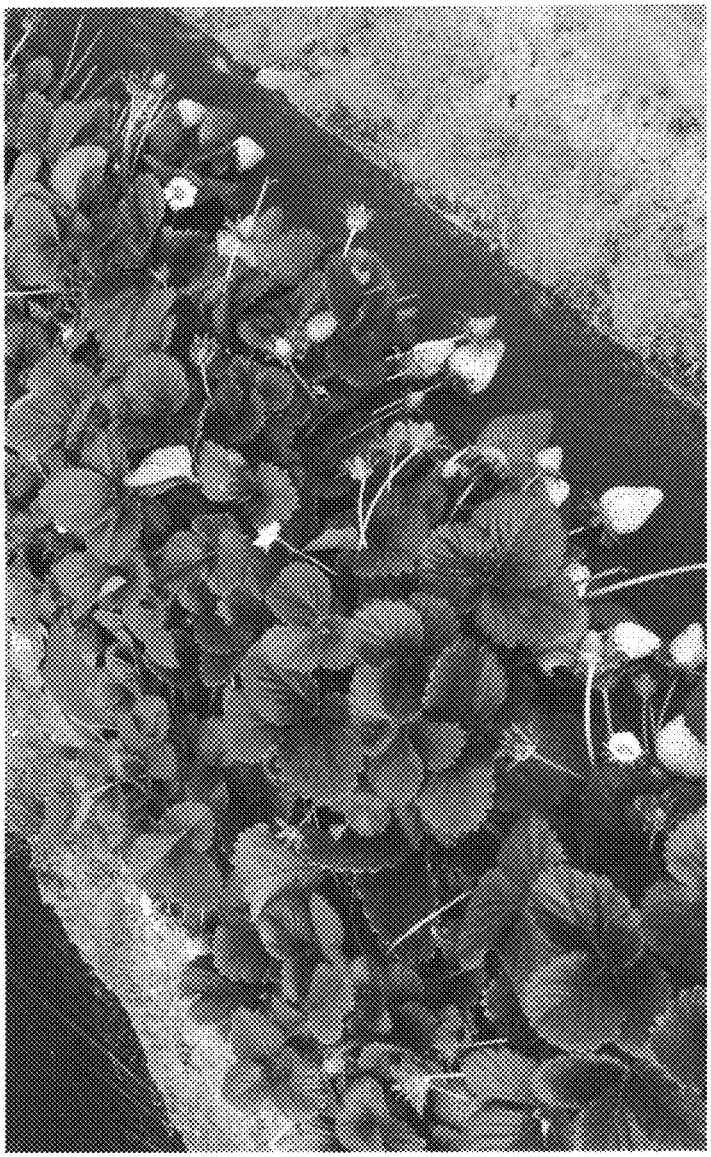

Botanical designation: *Fragaria* x *ananassa*.
Cultivar denomination: 'FS 1705'.

BACKGROUND OF THE INVENTION

The present Invention relates to a new and distinct cultivar of Strawberry plant, botanically known as *Fragaria* x *ananassa* and hereinafter referred to by the name 'FS 1705'.

The new Strawberry plant is a product of a planned breeding program conducted by the Inventor in Eck en Wiel, The Netherlands and Lepe, Spain. The objective of the breeding program was to develop new Strawberry plants with good fruit quality, ease of harvesting, high yield, large fruits and good postharvest longevity.

The new Strawberry plant originated from a cross-pollination by the Inventor during the summer of 2010 in Eck en Wiel, The Netherlands of a proprietary selection of *Fragaria* x *ananassa* identified as code designation S2009-639, not patented, as the female, or seed, parent with *Fragaria* x *ananassa* 'Calinda', disclosed in U.S. Plant Pat. No. 26,904, as the male, or pollen, parent. The new Strawberry plant was discovered and selected by the Inventor as a single plant from within the progeny of the stated cross-pollination in a controlled environment in Lepe, Spain in 2012.

Asexual reproduction of the new Strawberry plant by runner cuttings in a controlled environment at Eck en Wiel, The Netherlands since 2012 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FS 1705'. These characteristics in combination distinguish 'FS 1705' as a new and distinct Strawberry plant:

1. Compact, upright to semi-upright plant habit.
2. Moderately vigorous to vigorous growth habit.
3. Early and uniform fruit ripening.
4. Medium to large-sized conical fruits that are glossy and orange red in color.
5. Pleasant fruit aroma and sweet taste.
6. Excellent fruit postharvest longevity.

Plants of the new Strawberry differ primarily from plants of the female parent selection in the following characteristics:

1. Plants of the new Strawberry are more upright than and not as spreading as plants of the female parent selection.
2. Fruits of plants of the new Strawberry are conical in shape whereas fruits of plants of the female parent selection are long conical in shape.
3. Fruits of plants of the new Strawberry are orange red in color whereas fruits of plants of the female parent selection are orange in color.

Plants of the new Strawberry differ primarily from plants of the male parent, 'Calinda', in the following characteristics:

1. Plants of the new Strawberry are not as upright as plants of 'Calinda'.
2. Plants of the new Strawberry are more vigorous than plants of 'Calinda'.
3. Leaves of plants of the new Strawberry are lighter green in color than leaves of plants of 'Calinda'.
4. Fruits of plants of the new Strawberry are lighter in color than fruits of plants of 'Calinda'.

5. Fruits of plants of the new Strawberry are firmer than fruits of plants of 'Calinda'.

Plants of the new Strawberry can be compared to plants of *Fragaria* x *ananassa* 'Rociera', not patented. In side-by-side comparisons, plants of the new Strawberry differ primarily from plants of 'Rociera' in plant habit as plants of the new Strawberry are not as upright as plants of 'Rociera'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet (FIG. 1 of 2) is a side perspective view of typical fruiting plants of 'FS 1705' grown in a greenhouse environment.

Figure 2:
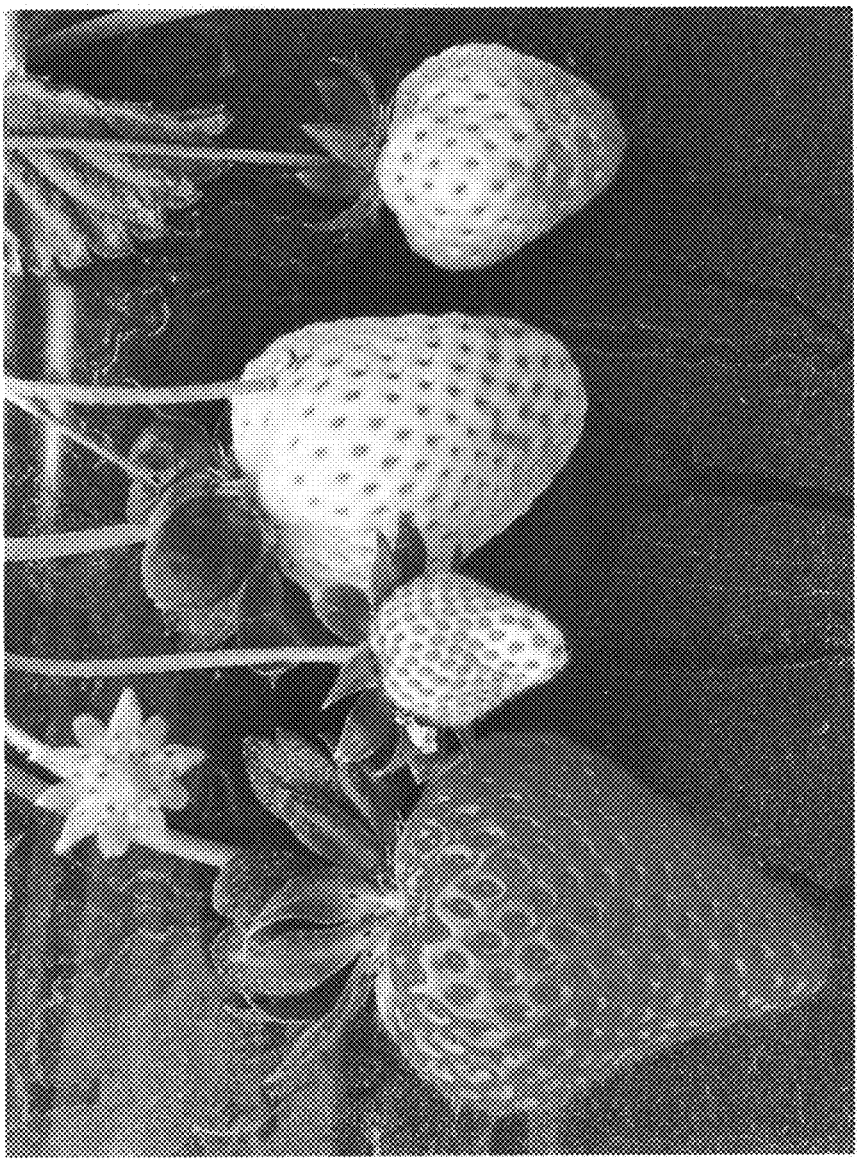

The photograph on the second sheet (FIG. 2 of 2) is a close-up view of typical developing and developed fruits of 'FS 1705'.

DETAILED BOTANICAL DESCRIPTION

The following observations and measurements describe plants grown in 4.7-liter containers with four plants per container from during the winter and spring in a glass-covered greenhouse in Eck en Wiel, The Netherlands and under cultural practices typical of commercial Strawberry production. During the production of the plants, day temperatures ranged from 10° C. to 24° C. and night temperatures ranged from 8° C. to 12° C. Plants were four months old when the photographs and the description were taken. In the following description, color references are made to The Royal Horticultural Society Colour Chart, 2001 Edition, except where general terms of ordinary dictionary significance are used.

Botanical classification: *Fragaria* x *ananassa* 'FS 1705'.

Parentage:

*Female, or seed, parent*.—Proprietary selection of *Fragaria* x *ananassa* identified as code designation S2009-639, not patented.

*Male, or pollen, parent*.—*Fragaria* x *ananassa* 'Calinda', disclosed in U.S. Plant Pat. No. 26,904.

Propagation:

*Type*.—By runner cuttings.

*Time to initiate roots, summer*.—About one to four days at soil temperatures about 15° C. and ambient temperatures about 17° C.

*Time to produce a rooted young plant, summer*.—About two to three weeks at soil temperatures ranging from 15° to 20° C. and ambient temperatures about 17° C.

*Root description*.—Medium in thickness, fibrous; typically cream white to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; compact, upright to semi- upright plant habit; leaves basal; moderately vigorous to vigorous growth habit; moderate growth rate; moderately densely foliated.

*Plant height*.—About 25 cm to 30 cm.

*Plant diameter*.—About 35 cm to 40 cm.

*Stolon texture*.—Sparsely pubescent.

*Stolon color*.—Close to 145A.

Leaf description:

*Arrangement and appearance*.—Basal rosette; compound with typically three leaflets per leaf; leaflets, concave, non-variegated and typically without anthocyanin when grown under normal and healthy growing conditions; little to no blistering observed.

*Leaflet length*.—About 9 cm to 12 cm.

*Leaflet width*.—About 8 cm to 11 cm.

*Leaflet shape*.—Broadly ovate.

*Leaflet apex*.—Obtuse to acute.

*Leaflet base*.—Obtuse to rounded.

*Leaflet margin*.—Crenate.

*Leaflet texture and luster, upper surface*.—Pubescent; moderately glossy to glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles*.—Length: About 9 cm to 15 cm. Diameter: About 2.5 mm to 5 mm. Texture, upper and lower surfaces: Pubescent; hairs orientated slightly outwardly. Color, upper and lower surfaces: Close to 145A.

*Stipules*.—Length: Medium about 1.4 cm to 2 cm. Color: Light green becoming brown to dark brown with development.

Flower description:

*Flower form and flowering habit*.—Rotate flowers arranged singly at lateral apices; flowers held upright and at about the foliar plane; flowers are self-fertile.

*Fragrance*.—None detected.

*Natural flowering season*.—Plants flower in from the end of January until the end of June in The Netherlands.

*Flower diameter*.—Medium to large, about 2.5 cm to 3.5 cm.

*Flower depth* (*height*).—About 5 mm to 10 mm.

*Petals*.—Arrangement: Single whorl of six petals; petals imbricate. Length: About 8 mm to 12 mm. Width: About 8 mm to 12 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155C. When opening and fully opened, lower surface: Close to 155C.

*Sepals*.—Arrangement and calyx description: Single whorl of eight to twelve sepals; calyx, star-shaped; calyx adherence is slightly raised; sepals are orientated upwards from the fruit. Calyx length: About 1 cm to 1.5 cm. Calyx diameter: About 1 cm to 2 cm. Length: About 5 mm to 8 mm. Width: About 3 mm to 5 mm. Shape: Lanceolate to ovate. Apex: Acute.

Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 2 cm to 5 cm. Diameter: About 1 mm to 2 mm. Strength: Strong. Aspect: About 90° from peduncle axis. Texture: Pubescent; hairs orientated slightly outwardly. Color: Close to 144B.

*Reproductive organs*.—Stamens: Quantity per flower: About 25. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Quantity: About two to three per truss; about 25 to 30 fruits develop per plant during the fruiting season; plants produce fruit from early March until mid-June in The Netherlands; fruit bearing non- remontant. Postharvest longevity: About seven to ten days at 7° C. Length: About 3 cm to 6 cm. Diameter: About 2 cm to 3.5 cm. Shape: Relatively, fruits are medium to large in size and are conical in shape; secondary are generally slightly more angular. Fruit weight per fruit, first quality: About 24.2 g. Fruit weight per plant, first quality: About 823 g. Firmness: Medium firm. Fragrance, taste: Pleasant; good balance between sweetness and acidity; nice aroma. Degrees brix: About 7.6. Luster: Uniformly glossy. Surface unevenness: Smooth. Color, surface: Close to 40A. Color, flesh: Close to 32B. Achene density: Medium. Achene position: Slightly below the fruit surface. Achene color: Close to 1B to 1C.

Pathogen and pest resistance: Plants of the new Strawberry have been observed to be resistant to *Phytophthora cactorum* and to be moderately resistant to *Sphaerotheca macularis* and *Verticillium dahliae*. To date, plants of the new Strawberry have not been observed to be resistant to pests and other pathogens common to Strawberry plants.

It is claimed:

1. A new and distinct Strawberry plant named 'FS 1705' as illustrated and described.

* * * * *